United States Patent [19]
Yoon

[11] Patent Number: 6,036,704
[45] Date of Patent: Mar. 14, 2000

[54] ANASTOMOSIS APPARATUS AND METHOD FOR ANASTOMOSING AN ANATOMICAL TUBULAR STRUCTURE

[76] Inventor: InBae Yoon, 11886 Farside Rd., Ellicott City, Md. 21042

[21] Appl. No.: 09/310,998

[22] Filed: May 13, 1999

[51] Int. Cl.$^7$ .................................................. A61B 17/04
[52] U.S. Cl. ............................................................. 606/153
[58] Field of Search ................................... 606/153, 151, 606/139, 213, 215, 218, 154, 157

[56] References Cited

U.S. PATENT DOCUMENTS

| | | | |
|---|---|---|---|
| 4,233,981 | 11/1980 | Schomacher | 606/153 |
| 4,294,255 | 10/1981 | Geroc | 606/153 |
| 4,523,592 | 6/1985 | Daniel | 606/154 |
| 5,250,058 | 10/1993 | Miller et al. | 606/154 |
| 5,336,233 | 8/1994 | Chen | 606/153 |
| 5,425,738 | 6/1995 | Gustafson et al. | 606/153 |
| 5,824,061 | 10/1998 | Quijano et al. | 623/1 |

*Primary Examiner*—Gary Jackson
*Attorney, Agent, or Firm*—Blank Rome Comisky & McCauley LLP

[57] ABSTRACT

A method for anastomosing an anatomical tubular structure that has an unhealthy section interposed between two healthy sections includes the steps of moving a tubular wall of the unhealthy section radially outwardly relative to a central axis and connecting the tubular walls of the two healthy sections together to form a junction. The unhealthy section of the anatomical tubular structure forms a toroid that is disposed about the junction. The anastomosis method can be performed without first cutting or removing the unhealthy section of any human or animal anatomical tubular structure. An anastomosis apparatus for anastomosing an anatomical tubular structure includes a first body member, a second body member and a connector device. Each body member has a hole formed therethrough with a diameter sized to receive the anatomical tubular structure in a close-fitting relationship and a slit that extends from the hole exteriorly of the body member. Each body member moves between a closed state wherein the body member circumscribes the anatomical tubular structure and an opened state wherein the body member separates at the slit a distance sufficient to receive the anatomical tubular structure. The connector device connects the first and second body members together after the anatomical tubular structure is received by the holes of the body members.

23 Claims, 9 Drawing Sheets

ANASTOMOSIS APPARATUS AND METHOD FOR ANASTOMOSING AN ANATOMICAL TUBULAR STRUCTURE

FIELD OF THE INVENTION

The present invention is directed to an anastomosis apparatus and a method for anastomosing an anatomical tubular structure. Particularly, the present invention is directed to an anastomosis apparatus and a method for anastomosing an anatomical tubular structure without connecting two free ends of the anatomical tubular structure together.

BACKGROUND OF THE INVENTION

Many different types of methods and devices have been developed for performing anastomosis of anatomical tubular structures such as veins, arteries, bowel and other tubular vessels within human and animal bodies. Generally, anastomosis is a connection between two anatomical tubular structures that have been separated from connecting tissue. Particularly, anastomosis is a surgical joining of two ducts, blood vessels or bowel segments to allow flow of fluid from one of the ducts, blood vessels or bowel sections to the other. In other words, conventional anastomosis connects two free ends of the ducts, blood vessels or bowel segments together.

U.S. Pat. No. 4,470,415 to Wozniak teaches a device and method for sutureless surgical anastomosis. A heat shrinkable sleeve is placed around two tubular members to be anastomosed and then shrunk to engage and maintain the two tubular members in an anastomotic relationship. The ends of the tubular members are everted over ferrules which are positioned on the ends of the tubular members.

U.S. Pat. No. 4,294,255 to Geroc teaches an intraluminal anastomosis device that includes complimentary, ring-shaped clamping and pinning members for end-to-end anastomosis of an anatomical tubular structure. Confronting faces of the members of the device have an annular, sharpened rim that is located at a radially innermost position. The confronting faces of the members also include an annular groove located radially outwardly of the rim. The annular groove includes a plurality of spaced, longitudinally extending openings that have radially inwardly projecting serrations. Toothed pins are retained in the openings to securely clamp the members and intervening tissue together.

U.S. Pat. No. 4,264,257 to Berggren et al. discloses a surgical instrument for performing anastomosis. The surgical instrument includes two clamps with each clamp arranged to support a fastening member. The fastening members are rings that have axially extending pins. The clamps are rotatably connected to the surgical instrument. The surgical instrument is actuated by moving the clamps toward each other to join the fasteners and vessels which are threaded onto the fastening members.

U.S. Pat. No. 3,606,888 to Wilkinson reveals a stapling apparatus for anastomosis of hollow viscera. An annular array of staples are set to join cut ends of a hollow viscus by everting the cut ends through and outwardly between a pair of opposed staple-setting split rings. The rings operate to staple the everted ends together. The rings are opened in order to remove them from the repaired viscus.

U.S. Pat. No. 4,624,255 to Schneck et al. discloses an apparatus for anastomosing a pair of severed blood vessel portions. The apparatus is a ring member that tethers the blood vessel portions thereto under radial stress with the intima of the blood vessel portions opposed. During surgery, the ring member is positioned around an end of one of the severed blood vessels portions and the blood vessel portions are tethered to the ring member at at least three spaced apart locations stressing the blood vessel portions radially outwardly in several directions to evert the intima and hold the intima of the two portions against each other.

In all of the references described above, anastomosis is performed in which two free ends of the vessel are connected together. For smaller vessels, connecting two free ends of the vessel together requires a highly skilled surgeon and is quite time consuming.

There is a need in the medical community to improve anastomosis of anatomical tubular structures. It would be beneficial to anastomose an anatomical tubular structure without having to connect two free ends of the tubular structure. It would be advantageous if the skill level of the surgeon could be lessened to perform successful anastomosis, particularly for smaller vessels. It would be beneficial if anastomosis could be performed in less time than is normally required to connect two free ends of the anatomical tubular structure. The present invention provides these benefits and advantages.

OBJECTS AND SUMMARY OF THE INVENTION

It is an object of the present invention to provide an apparatus and method for anastomosing an anatomical tubular structure without having to connect two free ends of the anatomical tubular structure.

Another object of the invention is to provide an apparatus and method for anastomosing an anatomical tubular structure for a surgeon who would not be required to connect two free ends of the anatomical tubular structure together.

Yet another object of the invention is to provide an apparatus and method for anastomosing an anatomical tubular structure in less time than is currently required.

Accordingly, an anastomosis apparatus and a method for anastomosing an anatomical tubular structure are hereinafter described. The anastomosis apparatus includes a first body member, a second body member and a connector device. Each of the first and second body members has a hole formed therethrough and a slit. The hole has a diameter sized to receive the anatomical tubular structure in a close-fitting relationship. The slit extends from the hole exteriorly of the body member. Each body member moves between a closed state and an opened state. In the closed state, the body member circumscribes the anatomical tubular structure. In the opened state, the body member separates at the slit a distance sufficient to receive the anatomical tubular structure. The connector device connects the first and second body members together when the anatomical tubular structure is received by holes of the body members.

For the method of the present invention, the anatomical tubular structure extends along a central axis and is defined by a tubular wall. The anatomical tubular structure has an unhealthy section interposed between two healthy sections of the anatomical tubular structure. The method of the present invention includes the steps of moving the tubular wall of the unhealthy section radially outwardly relative to the central axis and the step of connecting the tubular walls of the two healthy sections of the anatomical tubular structure together to form a junction. The unhealthy section of the anatomical tubular structure then substantially forms a toroid about the junction.

Other objects and advantages of the present invention will become apparent from the following description of the embodiments taken in conjunction with the accompanying drawings.

DETAILED DESCRIPTION OF THE EMBODIMENTS

Figure 1:
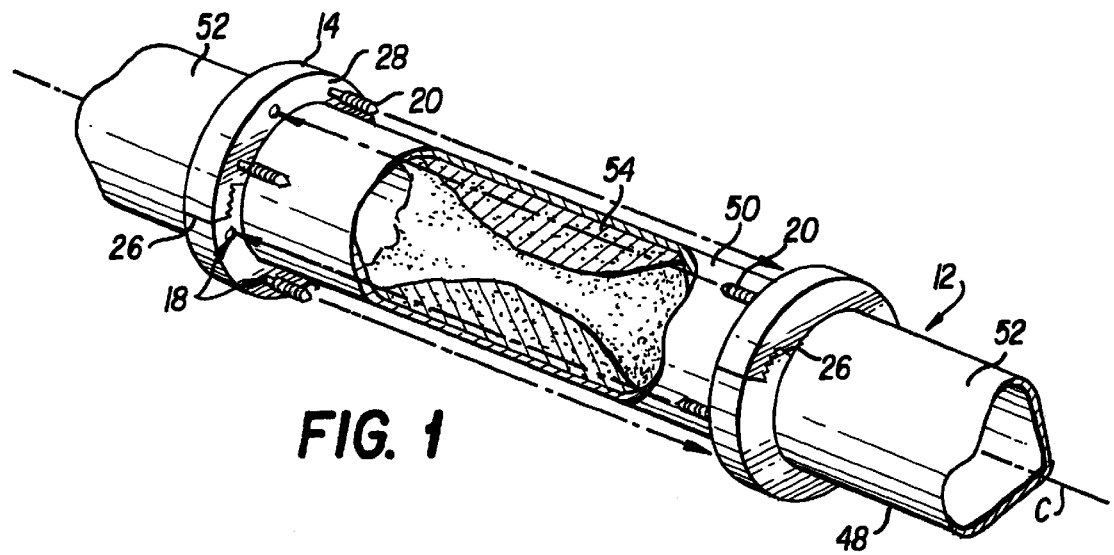
FIG. 1 is a perspective view of an anastomosis apparatus of the present invention secured onto an anatomical tubular structure illustrated as partially broken away.

An anastomosis apparatus 10 of the invention is generally introduced in FIGS. 1–8. As particularly shown in FIG. 1, the anastomosis apparatus 10 is used for anastomosing an anatomical tubular structure 12 such as a vascular or arterial vessel, bowel or other anatomical duct in human beings or animals. The anastomosis apparatus 10 of the invention includes a first body member 14, a second body member 16 and a connector device 18. The connector device 18 includes an alternating series of pins 20 and pin receiving holes 22 that are disposed in both the first body member 14 and the second body member 16, as described in more detail below.

Figure 2:
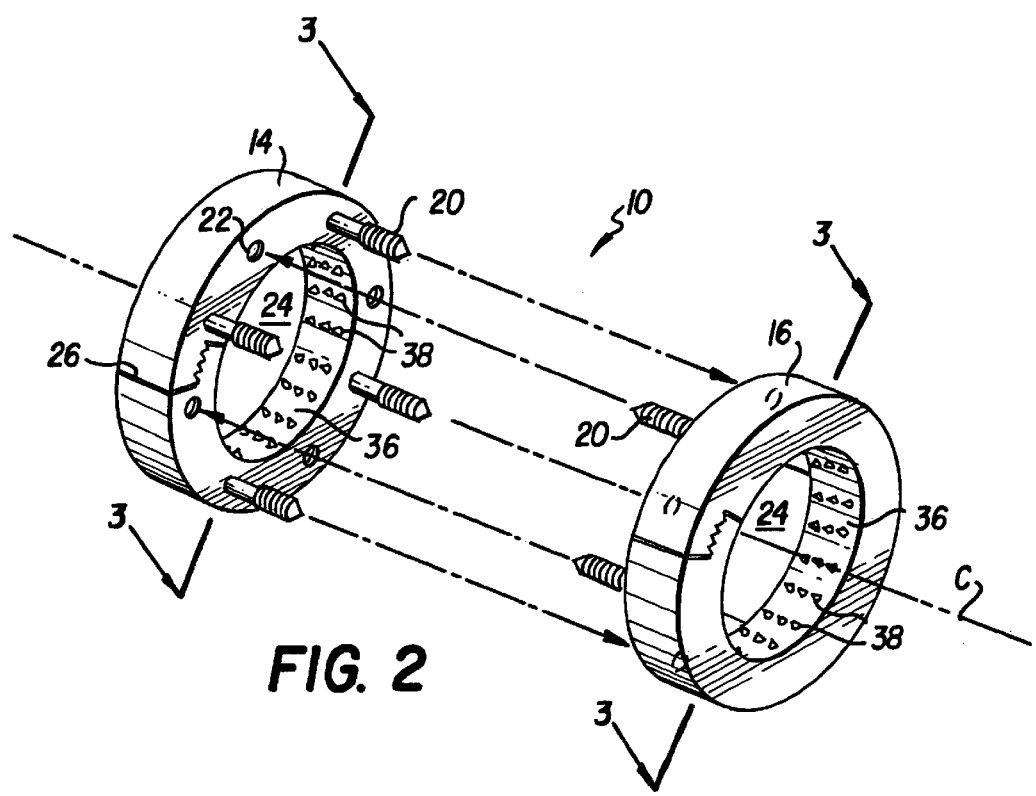
FIG. 2 is a perspective view of the anastomosis apparatus of the invention shown in FIG. 1.
Figure 3:
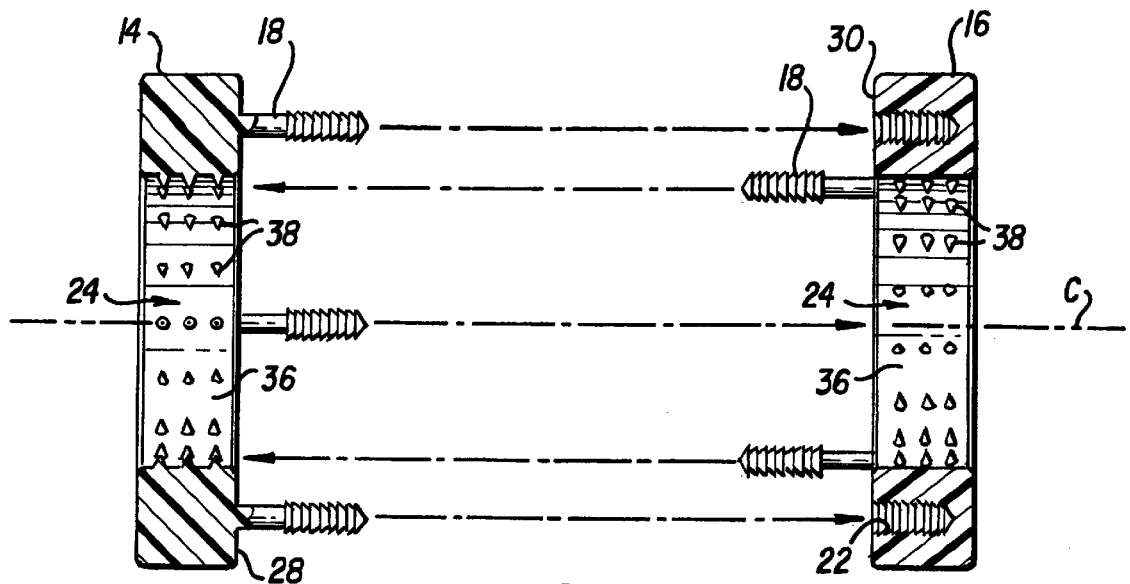
FIG. 3 is a side cross-sectional view of the anastomosis apparatus of the present invention shown in FIG. 2 taken along lines 3—3.
Figure 4:
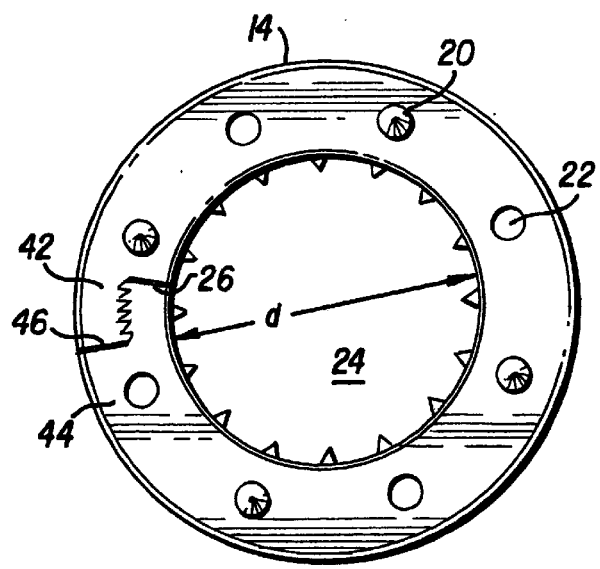
FIG. 4 is a front elevational view of one body member of the anastomosis apparatus of the present invention shown in a closed state.

In FIGS. 2 and 3, each of the first and second body members 14 and 16 has a hole 24 that is formed therethrough. Preferably, the hole 24 has a diameter "d" (FIG. 4) which is sized to receive the anatomical tubular structure 12 in a close-fitting relationship. Further, each one of the first and second body members 14 and 16 includes a slit 26, as best shown in FIGS. 1 and 4. In FIG. 4 the slit 26 extends from the hole 24 exteriorly of the first body member 14 in a zig-zag pattern.

Figure 6:
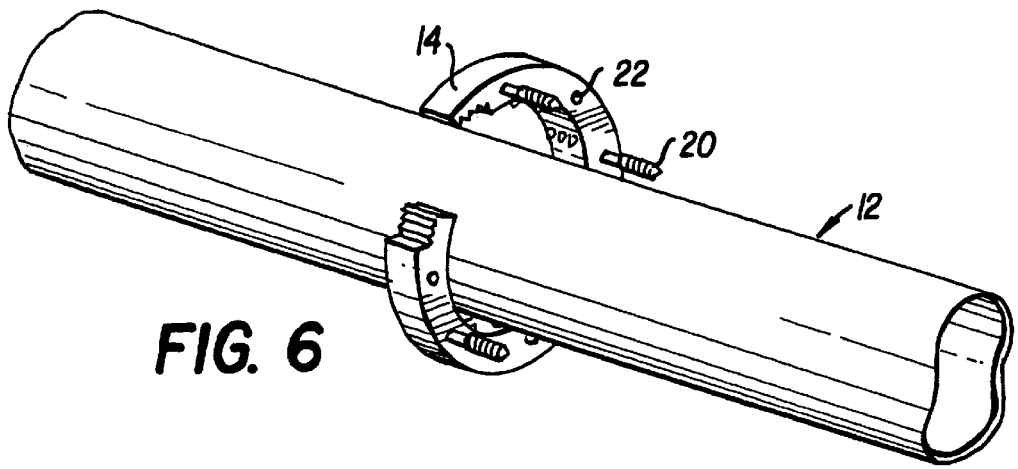
FIG. 6 is a perspective view of one body member of the anastomosis device of the present invention shown in an opened state for receiving the anatomical tubular structure.
Figure 5:
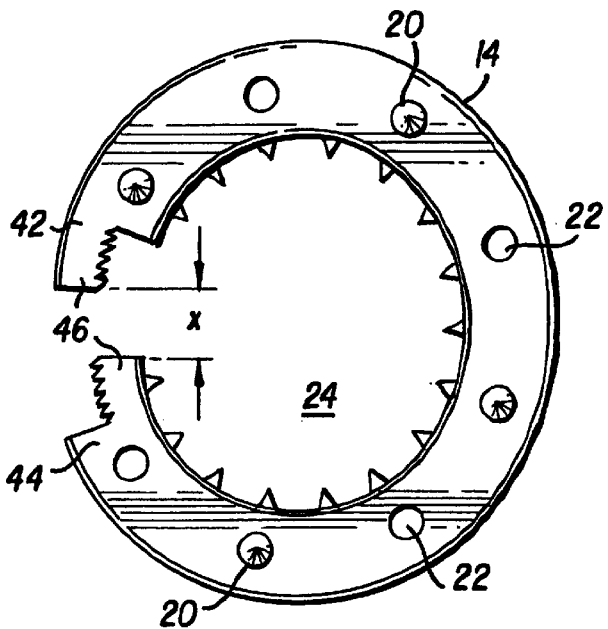
FIG. 5 is a front elevational view of one body member of the anastomosis apparatus shown in opened state.

Each of the first and second body members 14 and 16 is operative to move between a closed state as shown in FIGS. 1 and 4 and an opened state as shown in FIGS. 5 and 6. In the closed state, the first and second body members 14 and 16 circumscribe the anatomical tubular structure 12 as best shown in FIG. 1. In the opened state, each of the first and second body members 14 and 16 separates at the slit a distance "x" (FIG. 5) which is a sufficient distance for the first and second body members 14 and 16 to receive the anatomical tubular structure 12 as shown in FIG. 6. A skilled artisan would appreciate that the first and second body members 14 and 16 are substantially the same except that the alternating series of pins 20 and pin receiving holes 22 are arranged for matable engagement.

Figure 7:
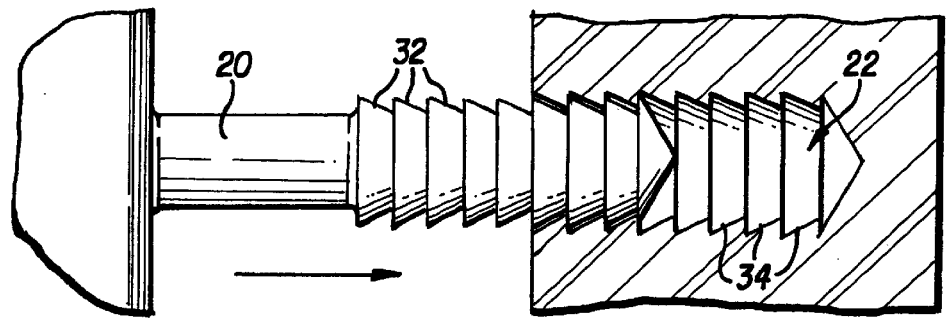
FIG. 7 is an enlarged cross-sectional side view of a pin and an opposing pin receiving hole of the anastomosis apparatus of the present invention shown in FIG. 3.

With reference to FIGS. 3 and 7, the connector device 18 is operative to connect the first and second body members 14 and 16 together. As discussed in more detail below, the connector device 18 connects the first and second body members 14 and 16 together when the anatomical tubular structure 12 is received through the respective holes 24 of the first and second body members 14 and 16. In FIG. 3, the first body member 14 has a first flattened surface 28 and the second body member 16 has a second flattened surface 30. The first and second flattened surfaces 28 and 30 respectively are facially opposed to each other as shown in FIG. 3 and extend radially relative to the anatomical tubular structure 12 when the first and second body members 14 and 16 circumscribe the anatomical tubular structure 12 as shown in FIG. 1.

With regard to the connector device 18, the pins 20 project from respective first and second flattened surfaces 28 and 30 and the pin-receiving holes 22 extend into respective first and second flattened surfaces 28 and 30. The pins 20 and the pin-receiving holes 22 are arranged so that the pins 20 extend from the first flattened surface 28 are aligned to slidably and retainably engage with the series of pin-receiving holes in the second flattened surface 30 of the second body member 16. The pins 20 extending from the second flattened surface 30 of the second body member 16 are aligned to slidably and retainably engage with the series of pin-receiving holes 22 of the first flattened surface 28 of the first body member 14. As illustrated in FIG. 7, each of the pins 20 includes a plurality of pin serrations 32 and each of the pin-receiving holes 22 includes a plurality of hole serrations 34 which are sized and adapted to receive and retain the pins 20. Although the serrations are illustrated in cross-section as right triangles, the serrations can be formed in any conventional configuration.

Again, with reference to FIGS. 2 and 3, each hole 24 of the respective ones of the first and second body members 14 and 16 is defined by a circumferential inner surface 36. Although not by limitation, each of the first and second body members 14 and 16 includes a plurality of protuberances 38 which project radially inwardly from the inner surface 36 relative to a central axis "C". Although not by way of limitation, each of the protuberances 38 is conically shaped.

Figure 8:
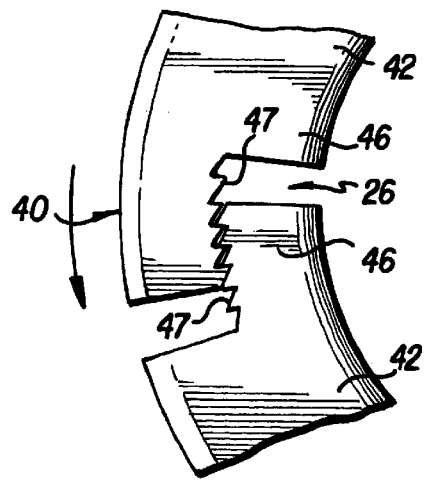
FIG. 8 is a partial enlarged front elevational view of two end portions of the anastomosis apparatus of the present invention showing an integral latch mechanism.

Preferably, each of the first and second body members 14 and 16 includes a latch mechanism 40 as shown in FIG. 8. The latch mechanism 40 operates to releasably retain the respective ones of the first and second body members 14 and 16 in the closed state. One of ordinary skill in the art would appreciate that the latch mechanism 40 illustrated in FIG. 8 is representative only and that many other types of latch mechanisms can be used to retain the body members in the closed state. However, it is preferred that the first and second body members 14 and 16 include opposing end portions 42 and 44 which are disposed opposite one another at the split 26. Each opposing end portion 42 and 44 includes an angled step portion 46 which is sized and adapted to matably engage with one another when respective one of the first and second body members are in the closed state. As shown in FIG. 8, facially opposing surfaces 47 include interlocking teeth that matably engage.

Although not by way of limitation, the first and second body members 14 and 16 are fabricated from a stiff, yet resilient material such as plastic or rubber so that the body members can move between the closed state and the opened state. Further, a stiff yet resilient material can be used so that the body members are biased toward the closed state. However, one of ordinary skill in the art would appreciate that the first and second body members 14 and 16 can be fabricated from a rigid material such as metal and a hinge can be provided so that the body members can move between the closed state and the opened state. Preferably, the first and second body members 14 and 16 are resiliently biased toward the closed state. Also, it is preferred that the first and second body members 14 and 16 are shaped as anuluses.

A method of the invention is hereinafter described. However, one of ordinary skill in the art would appreciate that the anastomosis apparatus 10 of the invention described above is a preferred apparatus for practicing the method of the invention and other devices can be used to practice the method of the invention without departing from the spirit and concept of the method of the invention described herein.

Figure 9:
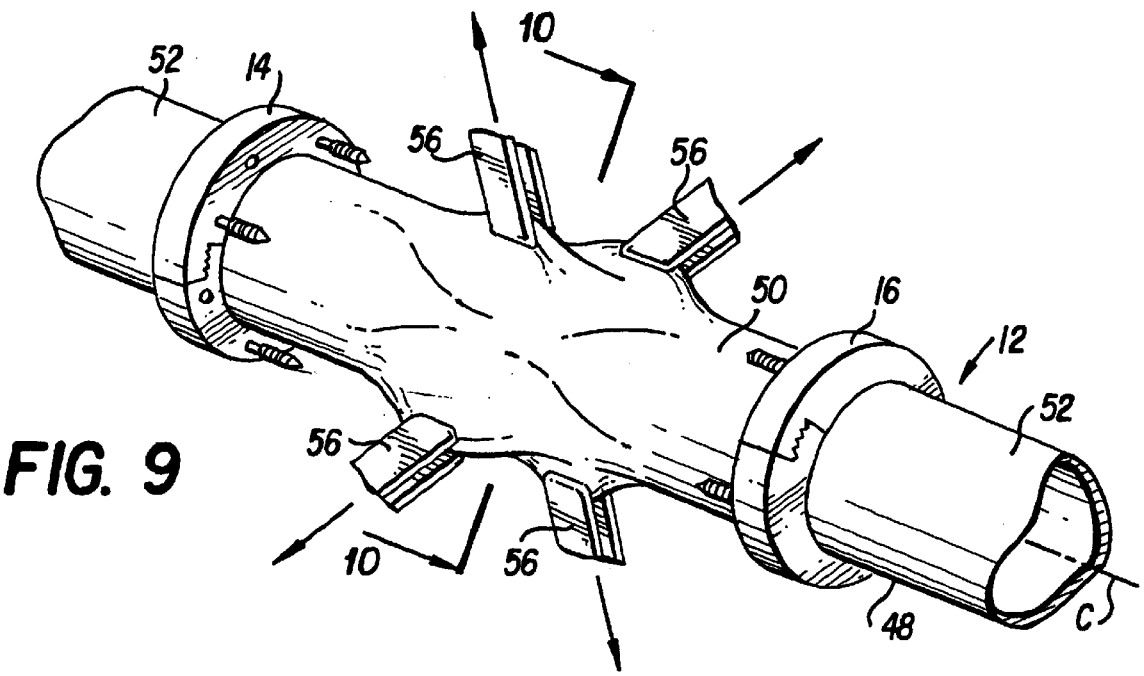
FIG. 9 is a perspective view of the anastomosis device of the present invention disposed on opposite ends of an unhealthy section of the anatomical tubular structure with the unhealthy section being moved radially outwardly by conventional pick-up instruments.
Figure 10:
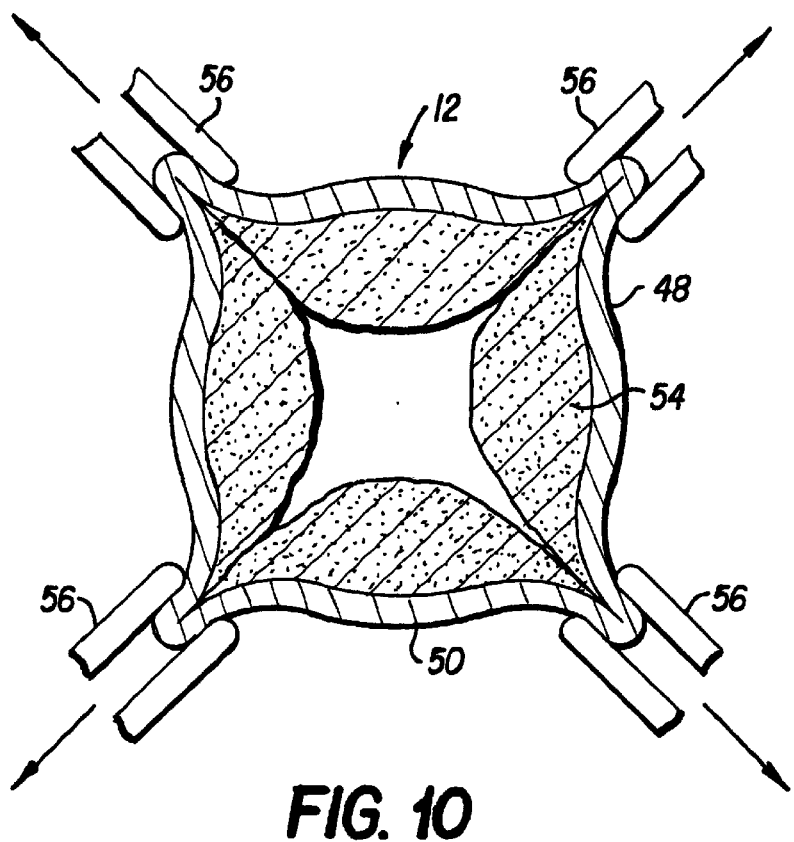
FIG. 10 is a cross-sectional view of FIG. 9.
Figure 11:
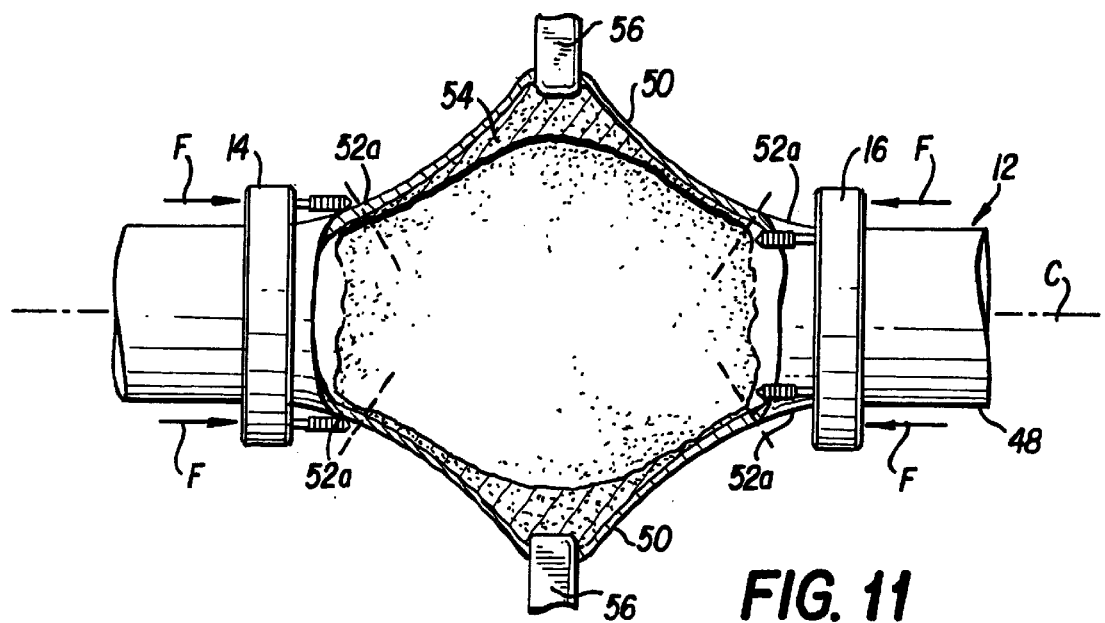
FIG. 11 is a side cross-sectional view as shown in FIGS. 9 and 10 before connecting the body members of the anastomosis apparatus of the present invention.
Figure 12:
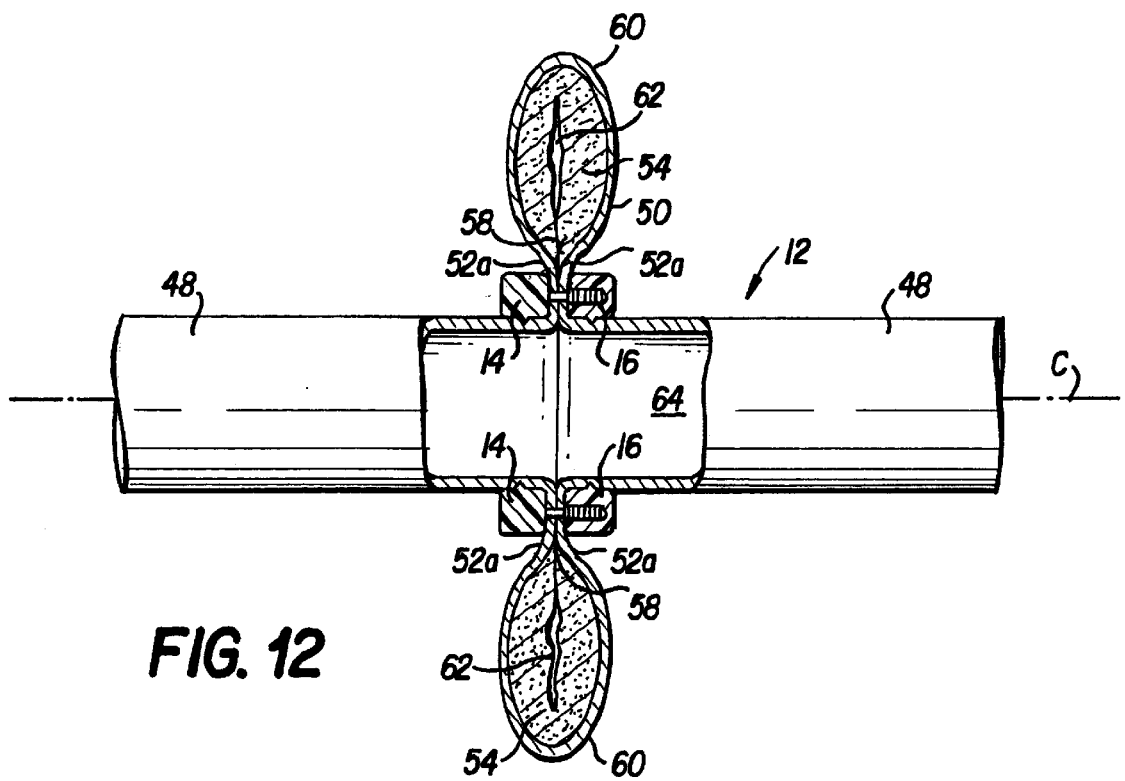
FIG. 12 is a side cross-sectional view of the anastomosis device of the present invention shown with the body members connected to each other achieving anastomosis.
Figure 13:
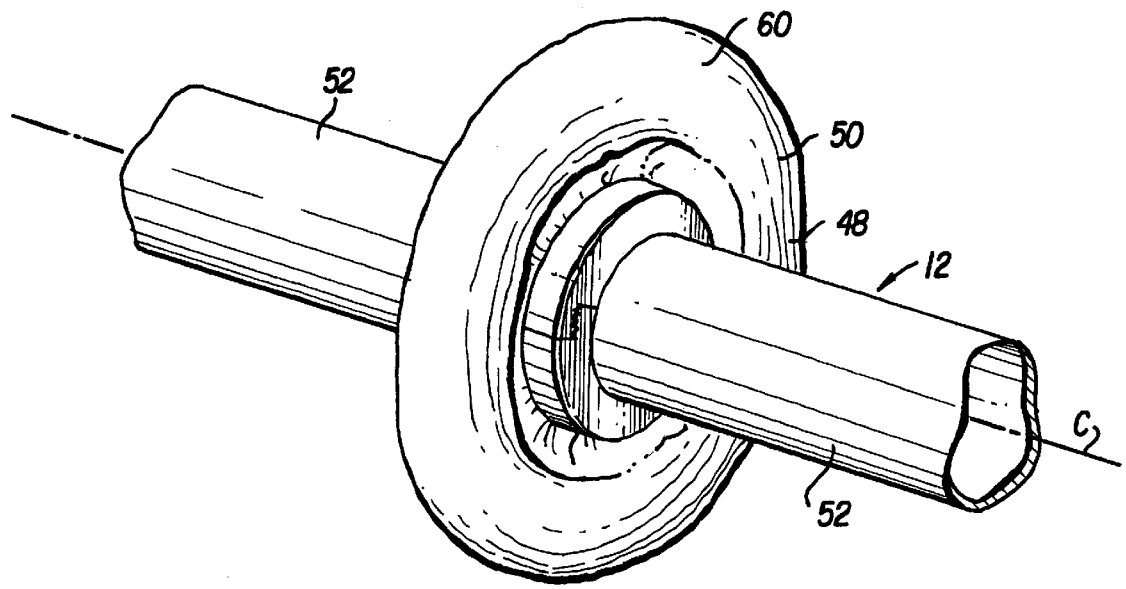
FIG. 13 is a perspective view of FIG. 12 illustrating a toroid of the tubular wall of the unhealthy section of the anatomical tubular structure surrounding the anastomosis apparatus of the present invention.

The method of the invention is introduced in FIGS. 9–13. The method of the invention is for anastomosing the anatomical tubular structure 12. The anatomical tubular structure 12 extends along the central axis "C" and is defined by a tubular wall 48. Typically, anastomosis is performed because the anatomical tubular structure 12 includes an unhealthy section that is interposed between two healthy sections 52 of the anatomical tubular structure 12. The description proceeds by way of example of an unhealthy section 50 of the anatomical tubular structure 12 as an occluded blood vessel that is occluded with a cholesterol deposit 54. As shown in FIGS. 9–11, the tubular wall 48 of the unhealthy section 50 of the anatomical tubular structure 12 is moved radially outwardly relative to the central axis "C" by a plurality of conventional pick-up instruments 56. By way of example only, the four conventional pick-up instruments 56 are used to grasp the tubular wall 48 of the unhealthy section 50 of the anatomical tubular structure 12 as shown in FIGS. 9–11. The next step connects the tubular walls 48 of the two healthy sections 52 of the anatomical tubular structure 12 together. More particularly, as shown in FIG. 12, the first and second body members 14 and 16 of the anastomosis apparatus 10 are disposed on the healthy sections 52 of the anatomical tubular structure 12 with the unhealthy section 50 disposed therebetween. As noted in FIG. 12, the first and second body members 14 and 16 of the anastomosis device 10 are positioned along the anatomical tubular structure 12 such that healthy portions 52a of the healthy sections 52 depicted adjacent the dashed lines in FIG. 11 are also disposed between the first and second body members 14 and 16. In FIG. 12, once the tubular walls 48 of the two healthy sections 52 are connected together by the first and second body member 14 and 16, a circumferential junction 58 of the healthy portions 52a of the anatomical tubular structure 12 is formed. The junction 58 is formed by compressing the healthy portions 52a of the anatomical tubular structure 12 together by connecting the first and second body members 14 and 16 together using pressing forces "F" illustrated in FIG. 11. Specifically, when the tubular walls of the healthy sections are connected together, the healthy portions 52a of the healthy sections 52 are moved in contact with each other. When the junction 58 is formed, the unhealthy section 50 substantially forms a toroid 60 that extends about the junction 58. The junction 58 forms a seal between a toroidal cavity 62 which is defined by the toroid 60 and a lumen 64 which is defined by the two connected healthy sections 52 of the anatomical tubular structure 12. It is appreciated that the toroid 60 illustrated as having a substantially tear-drop shaped cross-section can have other cross-sectional shapes.

As a result of the seal formed between the toroidal cavity 62 and the lumen 64, the toroid 60 is isolated from the two connected healthy sections 52 of the anatomical tubular structure 12. Thus, the toroid 60 is deprived of fluid communication with the two connected healthy sections 52 of the anatomical tubular structure 12.

Figure 14:
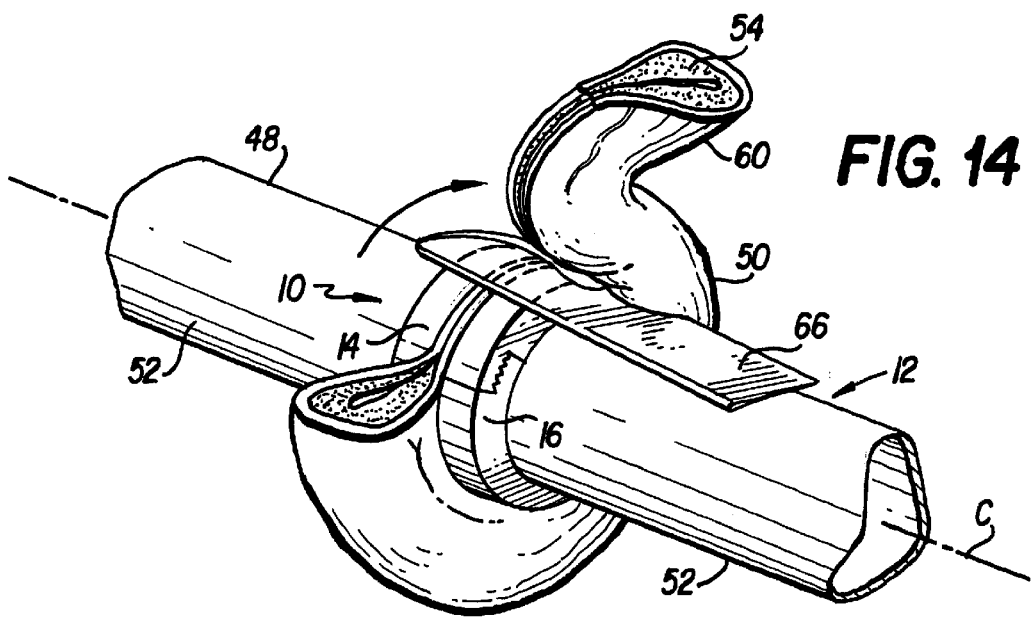
FIG. 14 is a perspective view similar to FIG. 13 illustrating a scalpel excising the toroid.

Although not by way of limitation, the toroid 60 can be excised from the anatomical tubular structure 12 by a scalpel 66 or other cutting device as shown in FIG. 14. However, a skilled artisan would appreciate that the toroid 60 could remain in place.

Figure 16A:
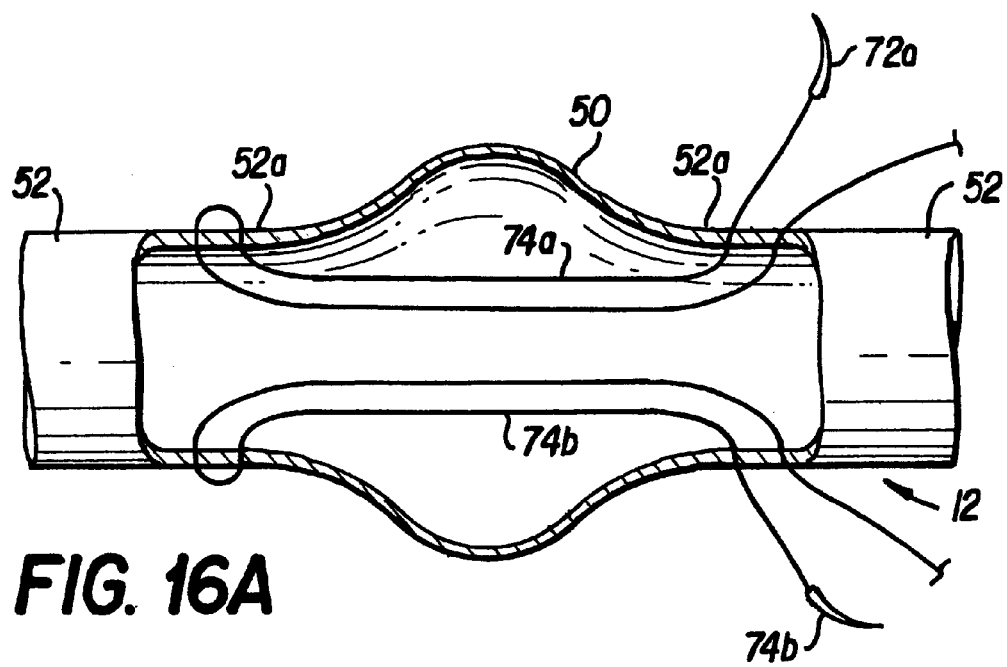
FIG. 16 A–C are cross-sectional views illustrating a suturing technique for performing the method of the present invention.
Figure 16B:
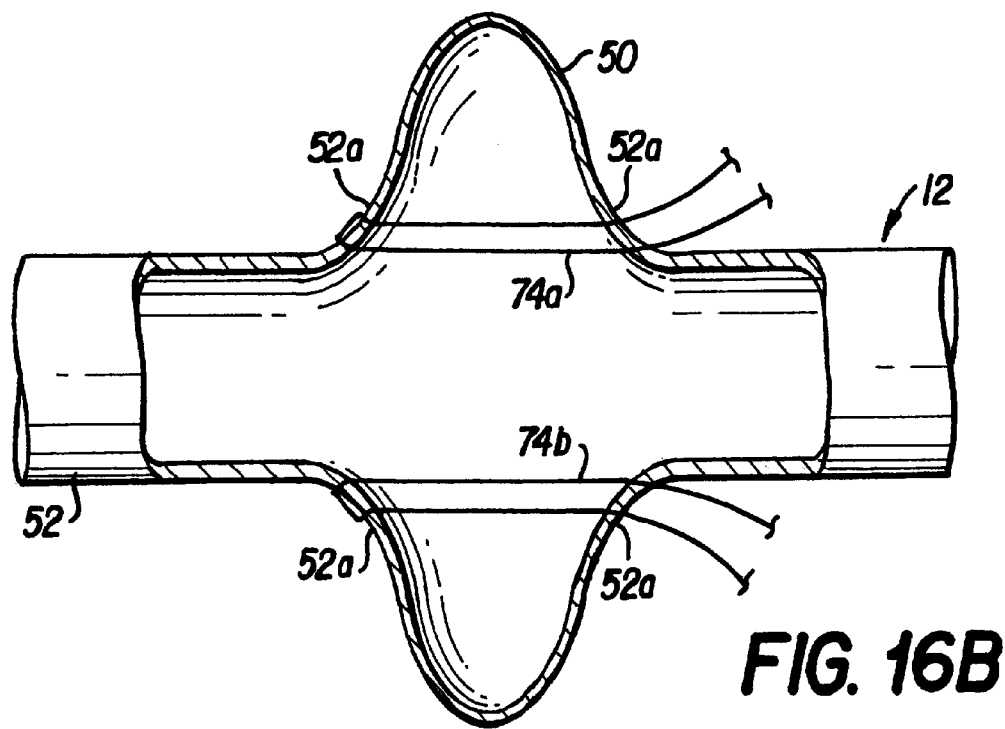
Figure 16C:
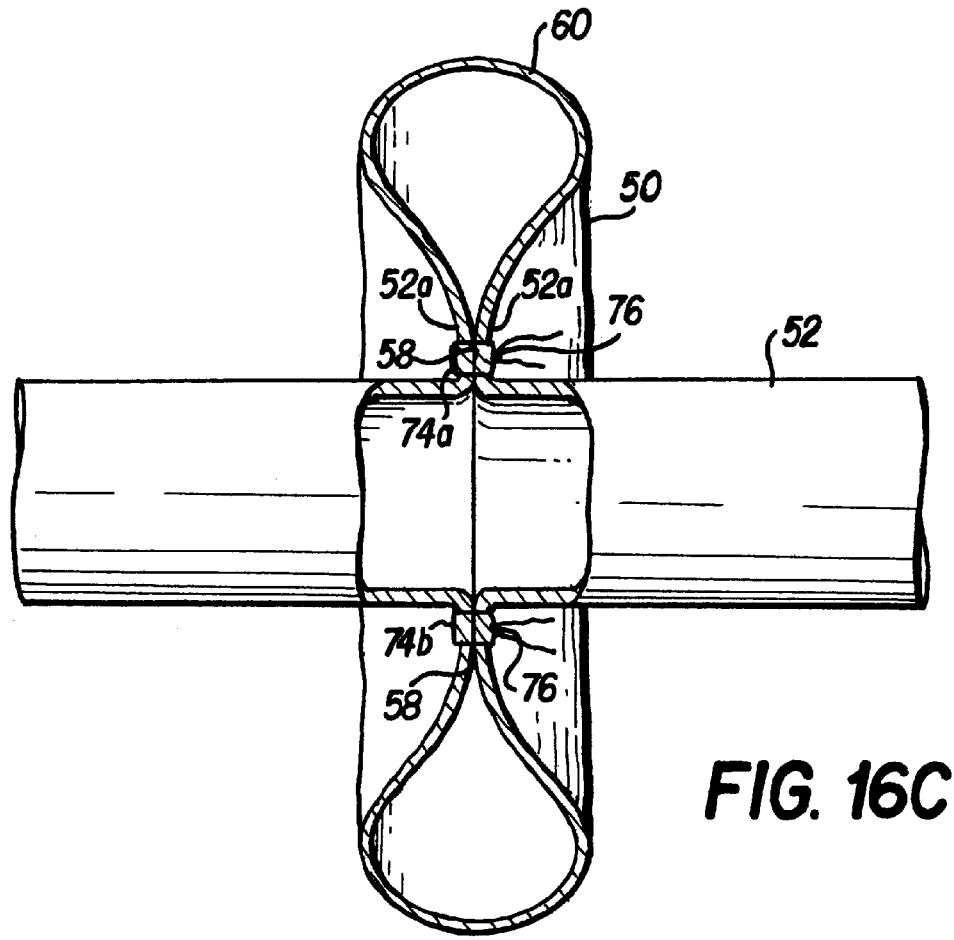
Figure 17:
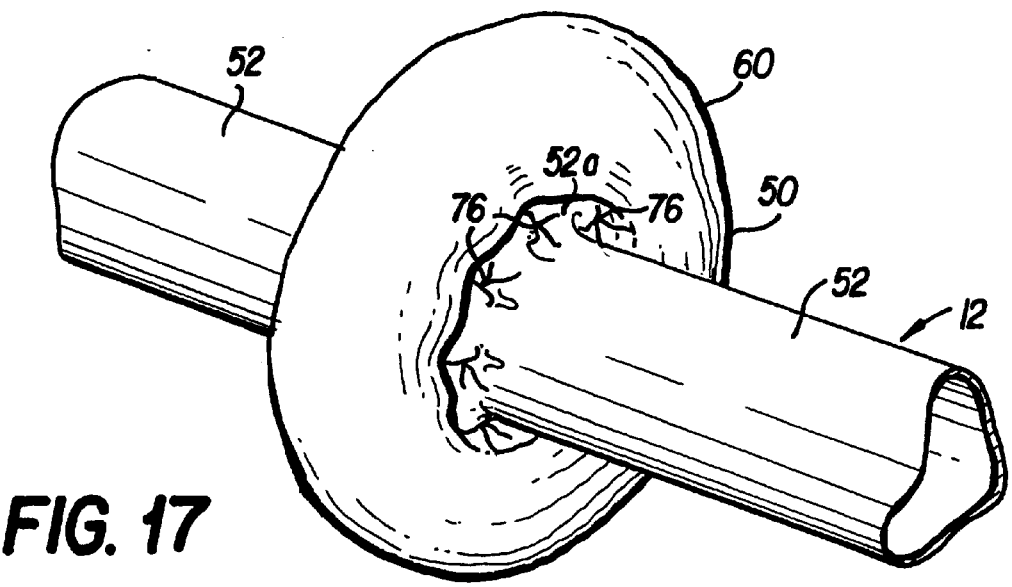
FIG. 17 is a perspective view illustrating connection of two healthy sections of the anatomical tubular structure by suture ties.

The anastomosis device 10 and the method of the invention are described by way of example only using an occluded anatomical tubular structure as shown in FIGS. 1 and 12. However, the unhealthy section 50 of the anatomical tubular structure 12 can be a diseased or damaged section such as an aneurysm as illustrated in FIGS. 15–17.

Figure 15:
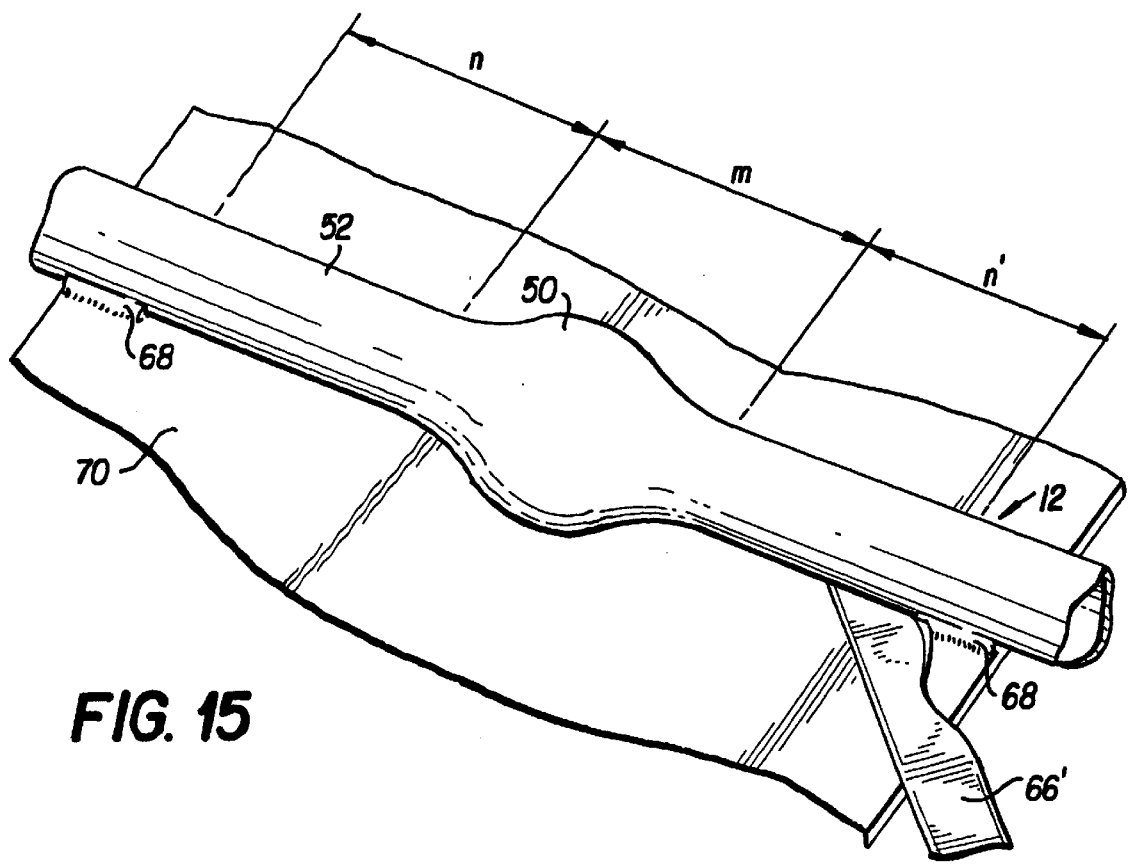
FIG. 15 is a prospective view of a diseased or damaged anatomical tubular structure being detached from connecting tissue.

In FIG. 15, the anatomical tubular structure 12 is detached from tissue 68 that connects the anatomical tubular structure 12 to a support structure 70. As known in the health care industry, a scalpel 66' or other cutting device is used to cut the tissue 68. Specifically, the anatomical tubular structure 12 is detached from the tissue 68 along the unhealthy section 50 and each of the two healthy sections 52. An amount of detachment of each of the healthy sections is preferred to be at least equal to a length "m" of the unhealthy section 50. Thus, a length "n" or "n'" of the healthy sections 52 is equal to or greater than the length "m" of the unhealthy section 50.

Once the appropriate length of the anatomical tubular structure 12 is detached from the tissue 68, the method of the invention is performed. With reference to FIGS. 16A–C, connection of the two healthy sections 52 of the anatomical tubular structure 12 is achieved by suturing. Suture needles 72a and 72b are connected to respective ones of sutures 74a and 74b and are looped through the healthy portions 52a of the anatomical tubular structure 12. Respective one of the sutures 74a and 74b are pulled so that the healthy portions 52a of the opposing healthy sections 52 contact each other. suture ties 76 are then made into each of the sutures as shown in FIG. 16C. FIG. 17 depicts the results of suturing using the method of the invention. Thus, connecting the tubular walls of the two healthy sections of the anatomical tubular structure together forms the junction 58 (FIG. 16C) so that the unhealthy section of the anatomical tubular structure extends radially outwardly from the junction to substantially define the toroid 60 which is disposed circumferentially about the junction.

Figure 18:
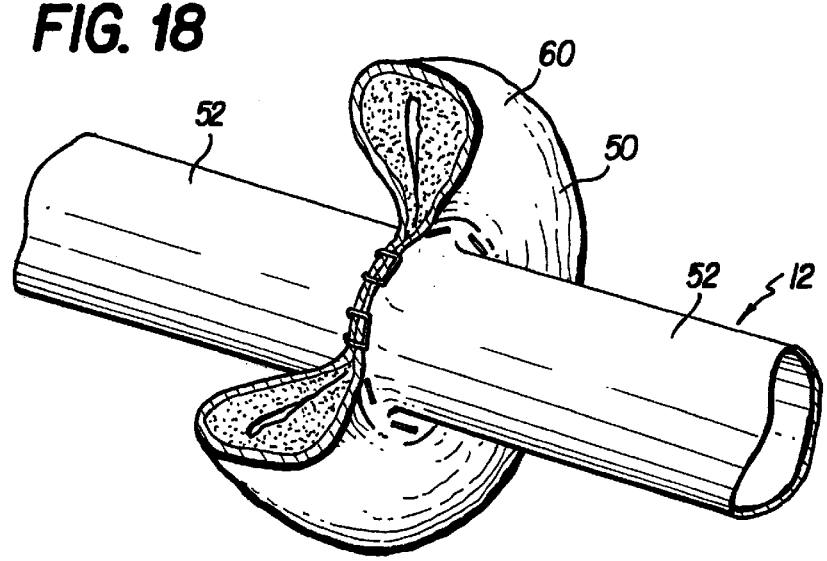
FIG. 18 is a prospective view illustrating connection of two healthy sections of the anatomical structure by staples or clips.

As shown in FIG. 18, connection of the two healthy sections 52 of the anatomical tubular structure 12 is achieved by stapling or clipping the healthy portions 52a of the opposing healthy sections 52 together. Conventional staples or clips 80 fabricated from a non-tissue reactive material are used.

As a result of the invention, anastomosis can be performed without having to connect two free ends of the anatomical tubular structure. Thus, the contents of the anatomical tubular structure can remain within it until anastomosis is completed. Further, the unhealthy section of the anatomical tubular structure can be either removed or remain in place at the discretion of the skilled artisan after performing the method of the invention. Also, because connecting two free ends of an anatomical tubular structure is no longer required, a lesser-skilled surgeon could perform the method of the invention. Further, the method of the invention requires less time to perform compared to connecting two free ends of the anatomical tubular structure by conventional anastomosis.

Although the embodiments of the invention have been specifically described herein, it will be apparent to those skilled in the art to which the invention pertains that other variations and modifications of the embodiments shown and described herein may be made without departing from the spirit and scope of the invention.

I claim:

1. A method for anastomosing an anatomical tubular structure extending along a central axis and defined by a tubular wall, the anatomical tubular structure having an unhealthy section interposed between two healthy sections, the method comprising the steps of:
   moving the tubular wall of the unhealthy section radially outwardly relative to the central axis; and
   connecting the tubular walls of the two healthy sections of the anatomical tubular structure together to form a junction whereby the unhealthy section of the anatomical tubular structure substantially defines a toroid disposed about the junction.

2. A method according to claim 1, wherein the junction is circumferential.

3. A method according to claim 1, wherein the junction forms a seal between a toroidal cavity defined by the toroid and a lumen defined by the two connected healthy sections of the anatomical tubular structure.

4. A method according to claim 1, wherein the unhealthy section is one of an aneurysm, a diseased section, a damaged section and an occluded section.

5. A method according to claim 1, wherein the step of connecting the tubular walls includes the step of moving end portions of the healthy sections of the anatomical tubular structure in contact with each other.

6. A method according to claim 1, wherein the toroid is isolated from the two connected healthy sections of the anatomical tubular structure.

7. A method according to claim 6, wherein the toroid is deprived of fluid communication with the two connected healthy sections of the anatomical tubular structure.

8. A method according to claim 1, further comprising the step of excising the toroid from the anatomical tubular structure.

9. A method according to claim 1, further comprising the step of detaching the anatomical tubular structure from tissue connected thereto wherein the anatomical tubular structure is detached from the tissue along the unhealthy section and each of the two healthy sections, an amount of detachment of each healthy section being at least equal to a length of the unhealthy section.

10. A method according to claim 1, wherein the step of connecting the two healthy sections of the anatomical tubular structure together is achieved by one of suturing, stapling and clipping.

11. An anastomosis apparatus for anastomosing an anatomical tubular structure, comprising:
   a first body member and a second body member, each body member having a hole formed therethrough with a diameter sized to receive the anatomical tubular structure in a close-fitting relationship and a slit extending from the hole exteriorly of the body member, each body member operative to move between a closed state wherein the body member circumscribes the anatomical tubular structure and an opened state wherein the body member separates at the slit a distance sufficient to receive the anatomical tubular structure; and
   a connector device operable to connect the first and second body members together when the anatomical tubular structure is received by the holes of the body members.

12. An anastomosis apparatus according to claim 11, wherein at least one of the first and second body members is shaped in a form of an annulus.

13. An anastomosis apparatus according to claim 11, wherein the first body member has a first flattened surface and the second body member has a second flattened surface, the first and second flattened surfaces being facially opposed to each other and extending radially relative to the anatomical tubular structure when the first and second body members circumscribe the anatomical tubular structure.

14. An anastomosis apparatus according to claim 13, wherein the connector device includes an alternating series of pins and pin receiving holes, the pins projecting from respective ones of the first and second flattened surfaces and the pin receiving holes extending into respective ones of the first and second flattened surfaces, the pins and pin receiving holes arranged such that the pins extending from the first flattened surface are aligned to slidably and retainably engage with the series of pin receiving holes of the second flattened surface and the pins extending from the second flattened surface are aligned to slidably and retainably engage with the series of pin receiving holes of the first flattened surface.

15. An anastomosis apparatus according to claim 14, wherein each of the pins includes a plurality of pin serrations and wherein each of the pin receiving holes includes a plurality of hole serrations sized and adapted to receive the pin serrations when respective ones of the pins are engaged with respective ones of the pin receiving holes.

16. An anastomosis apparatus according to claim 11, wherein each hole of respective ones of the first and second body members is defined by a circumferential inner surface and wherein at least one of the first and second body members include a plurality of protuberances projecting radially inwardly from the inner surface relative to the central axis.

17. An anastomosis apparatus according to claim 11, wherein at least one of the first and second body members includes a latch mechanism operative to releasably retain the at least one of the first and second body members in the closed state.

18. An anastomosis apparatus according to claim 17, wherein each of the first and second body members includes opposing end portions disposed opposite one another at the split, each end portion including an angled stepped portion sized and adapted to matably engage with one another when respective ones of the first and second body members are in the closed state.

19. An anastomosis apparatus according to claim 11, wherein each of the first and second body members is fabricated from a stiff yet resilient material.

20. An anastomosis apparatus according to claim 11, wherein each of the first and second body members is resiliently biased towards the closed state.

21. An anastomosis apparatus according to claim 11, wherein the each of the first and second body members is normally in the closed state.

22. An anastomosis apparatus for anastomosing an anatomical tubular structure defined by a tubular wall, the anatomical tubular structure having an unhealthy section interposed between two healthy sections, the anastomosis apparatus comprising:

means for connecting the tubular walls of the two healthy sections of the anatomical tubular structure together to form a junction when connected whereby the unhealthy section of the anatomical tubular structure extends radially outwardly from the junction to substantially define a toroid disposed circumferentially about the junction.

23. An anastomosis apparatus according to claim 22, wherein the means for connecting the tubular walls is suture ties, staples or clips.

* * * * *